United States Patent

Krishnan et al.

[11] Patent Number: 5,596,034
[45] Date of Patent: Jan. 21, 1997

[54] POLYCARBONATE COMPOSITIONS HAVING MOLD-RELEASE PROPERTIES

[75] Inventors: Sivaram Krishnan, Pittsburgh; James B. Johnson, Washington, both of Pa.; Robson Mafoti, Temple, Tex.

[73] Assignee: Bayer Corporation, Pittsburgh, Pa.

[21] Appl. No.: 524,820

[22] Filed: Sep. 7, 1995

[51] Int. Cl.$^6$ ............... C08K 5/10; C07C 67/00
[52] U.S. Cl. ............ 524/308; 524/311; 524/312; 524/313; 524/314; 524/315; 524/317; 524/245; 524/248; 524/250; 524/600
[58] Field of Search .................... 524/308, 311, 524/312, 313, 314, 315, 317, 245, 250, 600, 248

[56] References Cited

U.S. PATENT DOCUMENTS

| | | | |
|---|---|---|---|
| 3,784,595 | 1/1974 | Schirmer et al. | 260/18 TN |
| 3,836,499 | 9/1974 | Schirmer et al. | 260/31.2 R |
| 4,007,150 | 2/1977 | Adelmann et al. | 260/30.8 R |
| 4,131,575 | 12/1978 | Adelmann et al. | 260/17.4 R |
| 4,143,024 | 3/1979 | Adelmann et al. | 260/31.2 X |
| 4,446,268 | 5/1984 | Lee | 524/315 |
| 4,487,874 | 12/1984 | Lindner | 524/311 |
| 4,731,404 | 3/1988 | Haglock et al. | 524/308 |
| 4,868,236 | 9/1989 | O'Lenick, Jr. | 524/311 |
| 5,210,124 | 5/1993 | Hovatter et al. | 524/311 |

*Primary Examiner*—Paul R. Michl
*Assistant Examiner*—Olga Asinovsky
*Attorney, Agent, or Firm*—Joseph C. Gil; Aron Preis

[57] ABSTRACT

A thermoplastic molding composition having improved release properties is disclosed. The composition contains a polycarbonate resin and a mold release agent which is an ester conforming structurally to $$R + O - CO - R' - O - CO - R'']_m$$

where R is a member selected from the group consisting of glyceryl, trimethylol propyl and pentaerythrityl radicals, m is 2 to 4, R' is a $C_{8-20}$ hydrocarbon radical having a pendant alkyl group, and R" is the esterification residue of a $C_{1-24}$ aliphatic or an aromatic carboxylic acid.

9 Claims, No Drawings

POLYCARBONATE COMPOSITIONS HAVING MOLD-RELEASE PROPERTIES

FIELD OF THE INVENTION

The invention relates to thermoplastic molding compositions and in particular to compositions based on polycarbonates.

SUMMARY OF THE INVENTION

A thermoplastic molding composition having improved release properties is disclosed. The composition contains a polycarbonate and a mold release agent which is an ester conforming structurally to

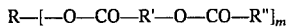

where R is a member selected from the group consisting of glyceryl, trimethylol propyl and pentaerythrityl radicals, m is 2 to 4, R' is a $C_{8-20}$ hydrocarbon radical having a pendant alkyl group, and R" is the esterification residue of a $C_{1-24}$ aliphatic or an aromatic carboxylic acid.

BACKGROUND OF THE INVENTION

Polycarbonates are widely used engineering thermoplastics because they feature an attractive set of physical and mechanical properties. A disadvantage is, however, associated with their processing in that they have poor release properties. In an injection molding application, this disadvantage translates to relatively long cycle times. Shorter cycle times have been attained by injection molding at higher temperatures and by using mold release agents. Improving the release properties of polycarbonate compositions by the incorporation of long chain aliphatic carboxylic acid esters of monohydric and trihydric alcohols has been reported in German published Specifications DOS 2,064,095 and 2,220,185. U.S. Pat. No. 4,007,150 disclosed the use of perfluoroalkane sulfonic acid amides and/or cyclic ammonium salts of such acids as mold release agents. Relevant technology has been disclosed in U.S. Pat. No. 3,784,595 which refers to polycarbonate molding compositions having improved release properties containing an ester of trihydric alcohol and a $C_{10-22}$-saturated aliphatic carboxylic acid. These esters are said to be effective mold release agents, without at the same time causing a measurable quality lowering degradation of the polycarbonate. Also relevant in this context is U.S. Pat. No. 3,836,499 which disclosed esters of monovalent $C_{10-35}$-alcohols and aliphatic saturated $C_{8-25}$-monocarboxylic acids. U.S. Pat. Nos. 4,131,575 and 4,143,024 disclosed relevant mold release technology entailing polycarbonate compositions and esters of saturated aliphatic carboxylic acid and respectively, 4-hydric to 6-hydric alcohols, and aromatic hydroxy compounds with from 1 to 6 OH groups. Also relevant is U.S. Pat. No. 4,446,268 which disclosed an asymmetric carboxylic acid ester having a long chain alcohol component said to have effective mold releasing properties in several thermoplastic resins, including polycarbonates.

Hydrogenated castor oil, has been reported to serve as an internal lubricant and to improve the heat stability of PVC compounds; it is also reported to be a processing aid/flow promoter for both polyethylene and polypropylene.

DETAILED DESCRIPTION OF THE INVENTION

Aromatic polycarbonates within the scope of the present invention include homopolycarbonates and copolycarbonates and mixtures thereof.

The suitable polycarbonates have a weight average molecular weight of 10,000 to 200,000, preferably 20,000 to 80,000 and their melt flow rate, per ASTM D-1238 at 300° C., is about 1 to about 65 g/10 min., preferably about 2 to 24 g/10 min. They may be prepared, for example, by the known diphasic interface process from a carbonic acid derivative such as phosgene and dihydroxy compounds by polycondensation (see German Offenlegungsschriften 2,063,050; 2,063,052; 1,570,703; 2,211,956; 2,211,957 and 2,248,817; French Patent 1,561,518; and the monograph H. Schnell, "Chemistry and Physics of Polycarbonates", Interscience Publishers, New York, N.Y., 1964, all incorporated herein by reference).

In the present context, dihydroxy compounds suitable for the preparation of the polycarbonates of the inventor conform to the structural formulae (1) or (2).

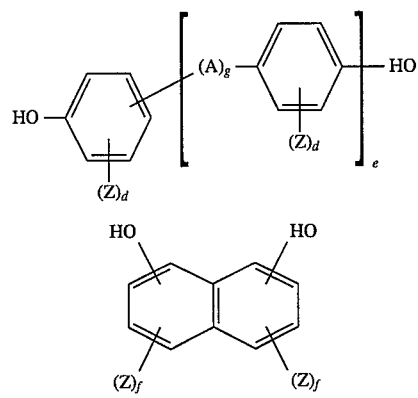

wherein

A denotes an alkylene group with 1 to 8 carbon atoms, an alkylidene group with 2 to 8 carbon atoms, a cycloalkylene group with 5 to 15 carbon atoms, a cycloalkylidene group with 5 to 15 carbon atoms, a carbonyl group, an oxygen atom, a sulfur atom, —SO—, or —SO$_2$— or a radical conforming to

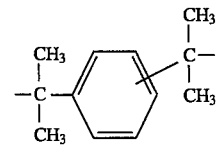

e and g both denote the number 0 to 1; Z denotes F, Cl, Br or $C_{1-4}$-alkyl and if several Z radicals are substituents in one aryl radical, they may be identical or different from one another;

d denotes an integer of from 0 to 4; and f denotes an integer of from 0 to 3.

Among the dihydroxy compounds useful in the practice of the invention are hydroquinone, resorcinol, bis-(hydroxyphenyl)-alkanes, bis-(hydroxyphenyl)-ethers, bis-(hydroxyphenyl)-ketones, bis-(hydroxyphenyl)-sulfoxides, bis-(hydroxyphenyl)-sulfides, bis-(hydroxyphenyl)-sulfones, and α,α-bis-(hydroxyphenyl)-diisopropylbenzenes, as well as their nuclear-alkylated compounds. These and further suitable aromatic dihydroxy compounds are described, for example, in U.S. Pat. Nos. 5,126,428; 5,104,723; 5,041,521; 5,034,457; 3,028,356; 2,999,835; 3,148,172; 2,991,273; 3,271,367; and 2,999,846, all incorporated herein by reference.

Further examples of suitable bisphenols are 2,2-bis-(4-hydroxyphenyl)-propane (bisphenol A), 2,4-bis-(4-hydroxyphenyl)-2-methylbutane, 1,1-bis-(4-hydroxyphenyl)-cyclohexane,α,α'-bis-(4-hydroxyphenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfide, bis-(3,5-dimethyl-4-hydroxyphenyl)-sulfoxide, bis-(3,5-dimethyl-4-hydroxyphenyl)-sulfone, dihydroxy-benzophenone, 2,4-bis-(3,5-dimethyl-4-hydroxyphenyl)-cyclohexane, α,α'-bis-(3,5-dimethyl4-hydroxyphenyl)-p-diisopropylbenzene and 4,4'-sulfonyl diphenol.

Examples of particularly preferred aromatic bisphenols are 2,2,-bis-(4-hydroxyphenyl)-propane, 2,2-bis-(3,5-dimethyl-4-hydroxyphenyl)-propane and 1,1-bis-(4-hydroxyphenyl)-cyclohexane.

The most preferred bisphenol is 2,2-bis-(4-hydroxyphenyl)-propane (bisphenol A).

The polycarbonates of the invention may entail in their structure units derived from one or more of the suitable bisphenols.

Among the resins suitable in the practice of the invention are included phenolphthalein-based polycarbonate, copolycarbonates and terpolycarbonates such as are described in U.S. Pat. Nos. 3,036,036 and 4,210,741, both incorporated by reference herein.

The polycarbonates of the invention may also be branched by condensing therein small quantities, e.g., 0.05 to 2.0 mol % (relative to the bisphenols) of polyhydroxyl compounds.

Polycarbonates of this type have been described, for example, in German Offenlegungsschriften 1,570,533; 2,116,974 and 2,113,374; British Patents 885,442 and 1,079,821 and U.S. Pat. No. 3,544,514. The following are some examples of polyhydroxyl compounds which may be used for this purpose: phloroglucinol; 4,6-dimethyl-2,4,6-tri-(4-hydroxyphenyl)-heptane; 1,3,5-tri-(4-hydroxyphenyl)-benzene; 1,1,1-tri-(4-hydroxyphenyl)-ethane; tri-(4-hydroxyphenyl)-phenylmethane; 2,2-bis-[4,4-(4,4'-dihydroxydiphenyl)]-cyclohexyl-propane; 2,4-bis-(4-hydroxy-1-isopropylidine)-phenol; 2,6-bis-(2'-dihydroxy-5'-methylbenzyl)-4-methylphenol; 2,4-dihydroxybenzoic acid; 2-(4-hydroxyphenyl)-2-(2,4-dihydroxyphenyl)-propane and 1,4-bis-(4,4'-dihydroxytriphenylmethyl)-benzene. Some of the other polyfunctional compounds are 2,4-dihydroxybenzoic acid, trimesic acid, cyanuric chloride and 3,3-bis-(4-hydroxyphenyl)-2-oxo-2,3-dihydroindole.

In addition to the polycondensation process mentioned above, other processes for the preparation of the polycarbonates of the invention are polycondensation in a homogeneous phase and transesterification. The suitable processes are disclosed in the incorporated herein by reference, U.S. Pat. Nos. 3,028,365; 2,999,846; 3,153,008; and 2,991,273.

The preferred process for the preparation of polycarbonates is the interfacial polycondensation process.

Other methods of synthesis in forming the polycarbonates of the invention such as disclosed in U.S. Pat. No. 3,912,688, incorporated herein by reference, may be used.

Suitable polycarbonate resins are available in commerce, for instance, Makrolon 2400, Makrolon 2600, Makrolon 2800 and Makrolon 3100, all of which are bisphenol based homopolycarbonate resins differing in terms of their respective molecular weights and characterized in that their melt flow indices (MFR) per ASTM D-1238 are about 16.5 to 24, 13 to 16, 7.5 to 13.0 and 3.5 to 6.5 g/10 min., respectively. These are products of Bayer Corporation of Pittsburgh, Pa.

Polycarbonate resins suitable in the practice of the invention are known and their structures and methods of preparation have been disclosed, for example, in U.S. Pat. Nos. 3,030,331; 3,169,121; 3,395,119; 3,729,447; 4,255,556; 4,260,731; 4,369,303 and 4,714,746 all of which are incorporated by reference herein.

The mold release agent in accordance with the present invention is an ester conforming structurally to

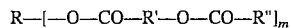

where R is a member selected from the group consisting of glyceryl, trimethylol propyl and pentaerythrityl radicals, m is 2 to 4, R' is a $C_{8-20}$ hydrocarbon radical having a pendant alkyl group, and R" is the esterification residue of a $C_{1-24}$ aliphatic or an aromatic carboxylic acid.

The mold release agent of the invention may be prepared by reacting, at a temperature above 100° C., a suitable polyhydric alcohol with an organic carboxylic acid in the presence of a catalyst, such as dibutyl tin oxide, sulfuric acid or a Lewis acid. By-product water formed in the reaction is continuously removed, using Dean and Stark setup to shift the esterification reaction towards completion. Measurements of acid number and FT-IR spectrophotometry may be used to monitor the progress of the reaction.

A suitable mold release agent in accordance with the invention has been prepared as described below.

The amount of the mold release agent to be added to the carbonate polymer is a positive amount which is sufficient to impart to the composition improved mold release property, the improvement determined in comparison to a corresponding composition which does not contain the inventive agent. Preferably, the composition of the invention contains about 0.1 to 2 percent of the mold release agent, said percent being relative to the weight of the composition.

The incorporation of the release agent into the polycarbonate follows standard techniques, including tumble blending the release agent with the polycarbonate pellets followed by extruding (at about 280°–300° C.) to form a strand which is then pelletized.

The method for determination of release force for the purpose of comparing the efficiencies of mold release agents is well known. Essentially, the injection cylinder of an injection molding machine, for instance, a 4 oz. Newbury, is equipped with a pressure transducer to measure and record the force during the ejection phase of molding a 90 mm diameter flat disc. The mold is characterized in that it has four intersecting 5 mm high by 1 to 2 mm thick tapered ribs laid out in a grid pattern. There are 4 ejector pins at the intersections of the ribs and 4 ejector pins along the perimeter of the disc. The mold is designed with minimum draft on the ribs to promote the tendency of the part to stick to the core. The moldings are injected at a melt temperature of 280° C. with a cycle time of 45 seconds between injections. The mold is maintained at a set point temperature of 79.5° C. The release force values reported below represent averages of the last 12 consecutive mold ejection hydraulic pressure values taken after the mold has stabilized, usually after 25 to 30 ejections.

The invention is further illustrated but is not intended to be limited by the following examples in which all parts and percentages are by weight unless otherwise specified.

EXAMPLES

A mold release agent within the scope of the invention has been prepared as described below:

A two liter flask was charged with 500 parts of a hydrogenated castor oil (Glycolube CW-1, from Lonza Inc.) having the following structure:

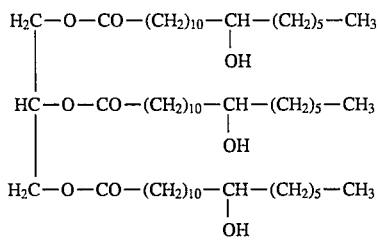

Nitrogen was bubbled through the flask and the temperature was raised to 120° C. while stirring. 453.92 parts of stearic acid were added and the temperature raised to 215° C. Water was collected in a receiving flask. After the atmospheric cycle, vacuum was slowly applied to the system and more water was distilled over (a total of 24 parts of the theoretical 28.8 parts of water were collected). The reaction was monitored by acid number (13.9) and FT-IR spectrophotometry. The reaction product, referred to below as Es-1, was collected.

In a second example, a two liter flask was charged with 355 parts of the same hydrogenated castor oil which was used in the previous example. Nitrogen was bubbled through the flask and the temperature was raised to 120° C. while stirring. 215.06 parts of stearic acid were added and the temperature raised to 215° C. Water was collected in a receiving flask. 106.4 parts of oleic acid were added and water was again collected in the receiving flask. After the atmospheric cycle, vacuum was slowly applied to the system and more water was distilled over (a total of 17.2 parts of the theoretical 20.4 parts of water were collected). The reaction was monitored by acid number (12.34) and FT-IR spectrophotometry. The reaction product was collected and used in the examples reported below, it is referred to below as Es-2.

Although demonstrated in reference to glycerol, mold release compounds within the scope of the present invention, based on other polyhydric alcohols, including pentaerythritol and trimethylolpropane may be prepared by analogous processes.

Compositions in accordance with the invention have been prepared and their mold release properties determined. The results are summarized below. In preparing the compositions, the carbonate polymer was a homopolycarbonate based on bisphenol-A and characterized in that its melt flow index was 18 g/10 min. as determined in accordance with ASTM D-1238 (Makrolon 2508 resin, a commercial product of Bayer Corporation); the mold releasing agents representative of the present invention are referred to below as Es-1 and Es-2.

Also prepared and evaluated were compositions containing pentaerythritol tetrastearate (referred to in the table as PETS), a prior art mold release agent. The compositions contained only polycarbonate resin and the indicated amounts of the mold releasing agents. Melt flow rate values in g/10 min. (MFR) were measured in accordance with ASTM D-1238 and the impact strength values (in ft lbs/in), notched Izod ⅛" and ¼" were determined in accordance with ASTM D-256. The results are presented below.

TABLE

|  | 1 | 2 | 3 | 4 | 5 | 6 |
|---|---|---|---|---|---|---|
| Release agent | none | PETS | Es-1 | Es-2 | Es-1 | Es-2 |
| amount (%) |  | 0.5 | 0.5 | 0.5 | 1.0 | 1.0 |
| MFR[1] | 18.4 | 16.2 | 17.8 | 20.0 | 20.8 | 21.8 |
| Impact strength[2] |  |  |  |  |  |  |
| ⅛" | 15.8 | 16.2 | 15.6 | 15.9 | 15.4 | 15.8 |
| ¼" | 1.7 | 1.5 | 1.5 | 1.4 | 1.3 | 1.3 |
| Release Force[3] (bars) | 22 | 19.0 | 18.0 | 17.0 | 17.0 | 16.0 |

[1] melt flow rate (g/10 min) measured in accordance with ASTM D-1238.
[2] Impact strength values (in ft lbs/in), notched Izod ⅛" and ¼" were determined in accordance with ASTM D-256.
[3] determined as described in the text above.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A thermoplastic molding composition comprising carbonate polymer and an effective amount of a mold releasing compound conforming to

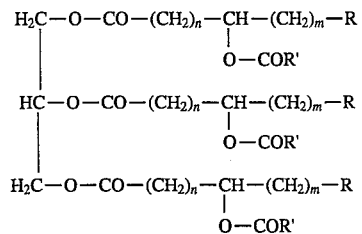

where n is 10 and m is an integer of about 2 to 10, R denotes a $C_{1-4}$-alkyl group or a $C_{6-10}$-aryl group and where R' denotes the esterification residue of at least one member selected from stearic acid and oleic acid.

2. The composition of claim 1 wherein said carbonate polymer is a homopolycarbonate based on bisphenol-A.

3. The composition of claim 1 wherein said effective amount is about 0.1 to 2 percent relative to the weight of said composition.

4. The composition of claim 2 wherein said effective amount is about 0.1 to 2 percent relative to the weight of said composition.

5. A molded article comprising the composition of claim 1.

6. The composition of claim 1 wherein said compound is the reaction product of glyceride of 12-hydroxystearic acid with at least one reactant selected from the group consisting of stearic acid and oleic acid.

7. The composition of claim 6 wherein said reactant is stearic acid.

8. The composition of claim 6 wherein said reactant is oleic acid.

9. A thermoplastic molding composition comprising carbonate polymer and an effective mold releasing complex ester forming by reacting a 12-hydroxystearate of glycerol, or a trimethylol propyl with stearic acid or oleic acid.

* * * * *